United States Patent
Ashkenazi et al.

(10) Patent No.: US 11,412,701 B2
(45) Date of Patent: Aug. 16, 2022

(54) INCREASED YIELD AND AMOUNT OF SOLUBLE SUGARS ALLOCATED TO FRUITS IN TOMATO PLANTS

(71) Applicant: Vilmorin & Cie, Paris (FR)

(72) Inventors: Varda Ashkenazi, Berurim (IL); Naama Barom, Berurim (IL); Shai Koussevitzky, Berurim (IL)

(73) Assignee: VILMORIN & CIE, Paris (FR)

( * ) Notice: Subject to any disclaimer, the term of this patent is extended or adjusted under 35 U.S.C. 154(b) by 526 days.

(21) Appl. No.: 16/088,674

(22) PCT Filed: Apr. 6, 2017

(86) PCT No.: PCT/EP2017/058262
§ 371 (c)(1),
(2) Date: Sep. 26, 2018

(87) PCT Pub. No.: WO2017/174727
PCT Pub. Date: Oct. 12, 2017

(65) Prior Publication Data
US 2020/0299787 A1    Sep. 24, 2020

(30) Foreign Application Priority Data
Apr. 7, 2016   (EP) .................................... 16305404

(51) Int. Cl.
| | | |
|---|---|---|
| A01H 5/08 | (2018.01) | |
| A01H 1/00 | (2006.01) | |
| A01H 6/82 | (2018.01) | |
| A01H 1/04 | (2006.01) | |

(52) U.S. Cl.
CPC ............... *A01H 6/825* (2018.05); *A01H 1/04* (2013.01); *A01H 5/08* (2013.01); *A01H 1/00* (2013.01)

(58) Field of Classification Search
None
See application file for complete search history.

(56) References Cited

FOREIGN PATENT DOCUMENTS

WO    WO 2011/026116 A1    3/2011

OTHER PUBLICATIONS

Monforte A. J. et al., Fine mapping of a quantitative trait locus (QTL) from Lycopersicon hirsutum chromosome 1 affecting fruit characteristics and agronomic traits: breaking linkage among QTLs affecting different traits and dissection of heterosis for yield, Theoretical and Applied Genetics, vol. 100, Feb. 1, 200, pp. 471-479.
Bernacchi D. et al. "Advanced backcross QTL analysis in tomato. I. Identification of QTLs of traits of agronomic importance from Lycopersicon hirsutum", Theoretical and Applied Genetics, vol. 97, Aug. 1998, pp. 381-397.
Bernacchi D. et al. "Advanced backcross QTL analysis in tomato. II. Evaluation of near-isogenic lines carrying single-donor introgressions for desirable wild QTL-alleles derived from *Lycopersicon hirsutum* and *L. pimpinellifolium*", Theoretical and Applied Genetics, vol. 97, Jul. 1998, pp. 170-180.
Hanson P.M. et al. "Performance of Solanum habrochaites LA1777 introgression line hybrids for marketable tomato fruit yield in Asia", Euphytica vol. 158, No. 1-2, May 16, 2007, pp. 167-178.
Grandillo S. & Tanksley S. "Advanced backcross QTL analysis: Results and Perspectives, in Tuberosa", In The Wake of Double Helix: From The Green Revolusition to the Gene Revolution: Proceedings of an International Congress, University of Bologna, Italy, May 27 to 31, 2003/Ed. R. Tuberosa, pp. 115-132.
Eshed Y. & Zamird D., "An introgression line population of Lycopersicon pennellii in the cultivated tomato enables the identification and the fine mapping of yield-associated QTL". Genetics Society of America 141:1174-1162. Nov. 1995.
Eshed Y. & Zamird D., "Less-than-additive epistatic interactions of quantitative trait loci in tomato". Genetics Society of America 143:1807-1817. Aug. 1996.

*Primary Examiner* — Phuong T Bui
(74) *Attorney, Agent, or Firm* — John P. White

(57) ABSTRACT

The invention relates to a *Solanum lycopersicum* plant comprising in its genome, on chromosome 1, introgressed sequences from *Solanum habrochaites*, wherein said introgressed sequences confer to the plant an improved phenotype corresponding to both an increased yield and an increased amount of soluble sugars allocated to fruits (Brix*Yield), with respect to a corresponding plant devoid of said sequences, and wherein said introgressed sequences are chosen from those present in the genome of a plant of the seeds ToPATYIELD NCIMB accession number 42567. The introgressed sequences are preferably characterized by defined alleles of different SNPs. on chromosome 1, inter alia allele T of SNP IL2_3605 (SEQ ID No. 9) and/or allele A of IL2_6411 (SEQ ID No. 12). The invention is also directed to parts of these plants with improved phenotype, as well as progeny, to the use of these plants for introgressing the improved phenotype in another genetic background, as well as to different methods for obtaining tomato plants or seeds with increased yield and brix*yield.

Figure 1:
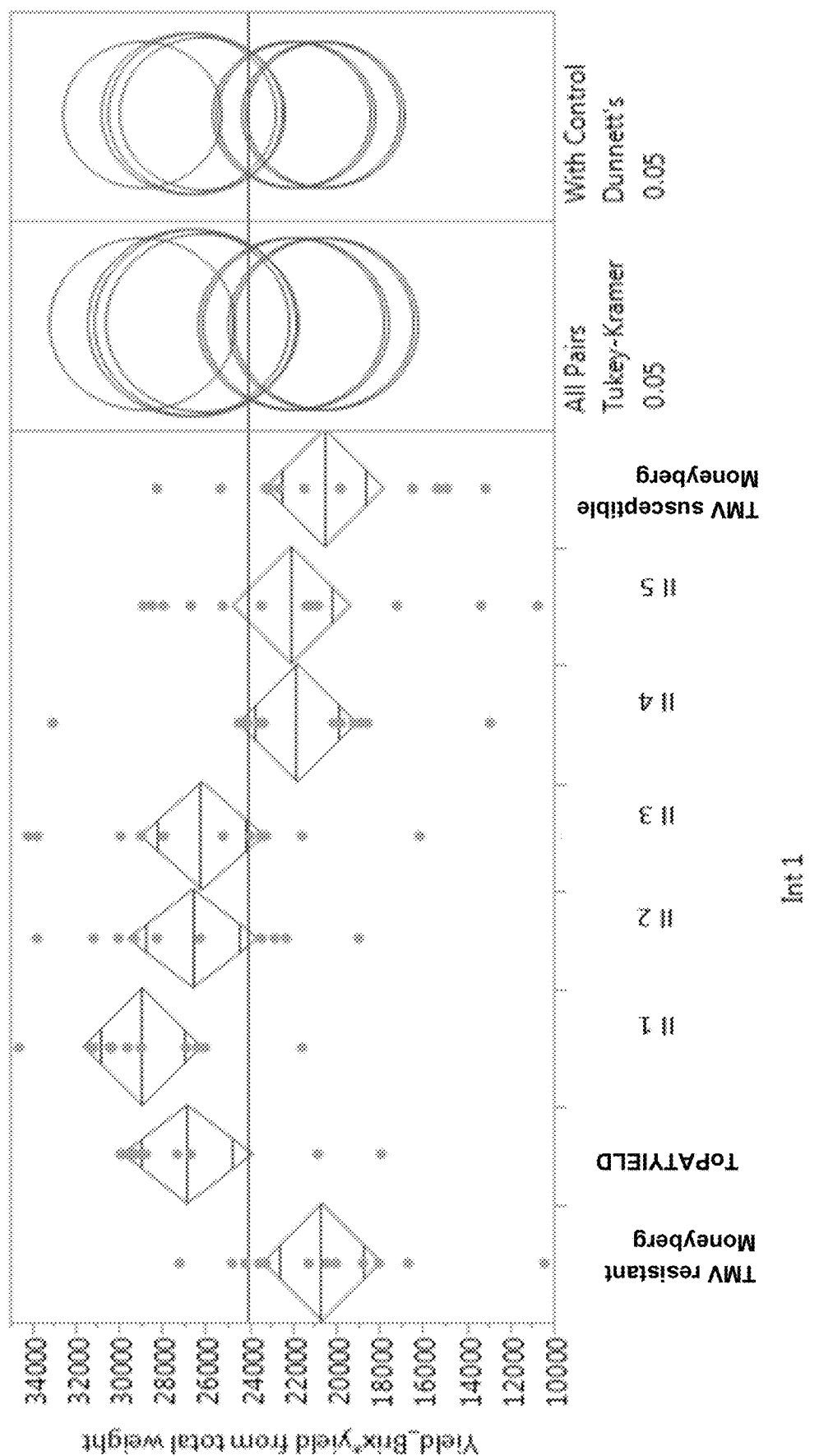

11 Claims, 2 Drawing Sheets
Specification includes a Sequence Listing.

```
                              SEQUENCE LISTING

<160> NUMBER OF SEQ ID NOS: 13

<210> SEQ ID NO 1
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
<223> OTHER INFORMATION: Allele associated with yield increase = T

<400> SEQUENCE: 1
agaaacaaat acttgttaac aacttaacat gatgtaatgg taaatatgaa cacatagaaa      60 ygggacaaa  aaataaaggt cttctaatgc tcttcagatg aagcaacact ggtaatgtta    120
g                                                                     121

<210> SEQ ID NO 2
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
<223> OTHER INFORMATION: Allele associated with yield increase = C

<400> SEQUENCE: 2
gagaaaaaga ccattagaca aagaaaaggt gttttgatag ctacggagaa aaagagaaag      60
yatagagaaa aaaagcaaaa cagggagatg aaagggtct ctaatgggag atccattccc     120
t                                                                     121

<210> SEQ ID NO 3
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
<223> OTHER INFORMATION: Allele associated with yield increase = C

<400> SEQUENCE: 3
ctggacaatt tagagctgaa tcttgatatt ctgccaattg ctatggtaat tgcagcatca      60
yaagaagctc aaaggcttaa ggcttggaga tttacttcat ggagtggggg gagattatgg    120
t                                                                     121

<210> SEQ ID NO 4
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
```

<223> OTHER INFORMATION: Allele associated with yield increase = G
<220> FEATURE:
<221> NAME/KEY: misc_feature
<222> LOCATION: (62)..(62)
<223> OTHER INFORMATION: n is a, c, g, or t

<400> SEQUENCE: 4
gtaatagaga aactgaaaga aaaaagggac aaaaatcaag ctgtcccggc atttactctt     60
knttttctac cagctttctc tacttttgtc tgatcttacg aaatgtaacc gcttcactca    120
t                                                                    121

<210> SEQ ID NO 5
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
<223> OTHER INFORMATION: Allele associated with yield increase = G

<400> SEQUENCE: 5
tgtctacaaa atgtgggagg tacaagagg gatttgattt tagtgctgag agagtgacta     60
raagtattga tgagagcttg gagaggctgc agcttgatta tgttgatatg ttacaatgtc    120
a                                                                    121

<210> SEQ ID NO 6
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
<223> OTHER INFORMATION: Allele associated with yield increase = A

<400> SEQUENCE: 6
catcaaaatc cagaacaagg aaatgaaacg aagcttctta gattgttctt ctgaagattg     60
rtccaactat tagtttggcc tacttacaag ttaccgatta acttaagctt aggaagcgaa    120
t                                                                    121

<210> SEQ ID NO 7
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
<223> OTHER INFORMATION: Allele associated with yield increase = G

<400> SEQUENCE: 7
cacaataagg taaacatatc atgcagtttg ctggttttga ctcttagatt gagcagacaa     60 kaggggttg ctgaggtggt aagcactctt cacctccaac accaaggttg ctggtagcaa    120
a                                                                    121

<210> SEQ ID NO 8
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
<223> OTHER INFORMATION: Allele associated with yield increase = T

<400> SEQUENCE: 8
actcatcagc aaaaggaaca gaatcttggc ttctgctcct gtttcttcac ccttcacttc    60
yccaaatgaa gagtccgaaa aagctaagtt agctcaggtt gccaaaagac tactgaatac   120
t                                                                  121

<210> SEQ ID NO 9
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
<223> OTHER INFORMATION: Allele associated with yield increase = T

<400> SEQUENCE: 9
cattagagca tctggtggat tcagaaattc tttcactaaa gctcatggaa tttcaaacac    60
kattggaatc atccttcttc tggtatatcc agtctgggca ttgattctcc actttctata   120
a                                                                  121

<210> SEQ ID NO 10
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
<223> OTHER INFORMATION: Allele associated with yield increase = G

<400> SEQUENCE: 10
atttgtattt catcgtagca agtcagaagt gtatttctgc ttgaaatgtt ttttatgtgc    60
rttgattagt gaaaatacag aatactttct aatggtacac aaaattatttt tctttgtcga   120 a                                                                  121

<210> SEQ ID NO 11
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
<223> OTHER INFORMATION: Allele associated with yield increase = C

<400> SEQUENCE: 11
tgtaatataa tatgcttcaa cagtatttat tcaacatata gccattgata tcattcaaac    60
maagcactcc cagtttcgca tagaggtacc atttaaccaa actggaggaa taaattatct   120
c                                                                  121

<210> SEQ ID NO 12
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
<223> OTHER INFORMATION: Allele associated with yield increase = A

<400> SEQUENCE: 12
tcaggaaact cttcttaatc tgctattgcg gaattatctt cactacaact tgtacgatca    60
mgcagagaaa ttgaggtcaa aggcccccca ttttgaagct cattcaaatc agcagttctg   120
c                                                                  121

```
<210> SEQ ID NO 13
<211> LENGTH: 121
<212> TYPE: DNA
<213> ORGANISM: Lycopersicon esculentum
<220> FEATURE:
<221> NAME/KEY: Polymorphism
<222> LOCATION: (61)..(61)
<223> OTHER INFORMATION: Allele associated with yield increase = T

<400> SEQUENCE: 13
ttttcatagg aaaaaattgg aggtttacaa tgaggtgctt cggaggctta aagaagaatc      60
ygacaataac gacactttac aatctgcttt tgacgatgaa ctttgggctc atttcaatcg     120
c                                                                    121
```

INCREASED YIELD AND AMOUNT OF SOLUBLE SUGARS ALLOCATED TO FRUITS IN TOMATO PLANTS

CROSS-REFERENCE TO RELATED APPLICATIONS

This application is a § 371 national stage of PCT International Application No. PCT/EP2017/058262, filed Apr. 6, 2017, claiming priority of European Patent Application No. 16305404.2, filed Apr. 7, 2016, the contents of each of which are hereby incorporated by reference into the application.

REFERENCE TO A SEQUENCE LISTING

This application incorporates-by-reference nucleotide and/or amino acid sequences which are present in the file named "180926_90686_Sequence_Listing_CAE.txt", which is 5.67 kilobytes in size, and which was created Sep. 26, 2018 in the IBM-PC machine format, having an operating system compatibility with MS-Windows, which is contained in the text file filed Sep. 26, 2018 as part of this application.

The present invention relates to the increase of yield in plants of *Solanum lycopersicum*, also known as *Lycopersicum esculentum*. According to the invention, the yield increase is provided by DNA sequences, introgressed from *S. habrochaites*, also known as *Lycopersicon hirsutum* at corresponding specific loci in the genome of a *S. lycopersicum* plant. The introgressed sequences can be present homozygously or heterozygously in the genome of the *S. lycopersicum* plant, and they confer increased yield to the said *S. lycopersicum* plant.

BACKGROUND OF THE INVENTION

All cultivated and commercial forms of tomato belong to a species most frequently referred to as *Lycopersicon esculentum* Miller. *Lycopersicon* is a relatively small genus within the extremely large and diverse family Solanaceae which is considered to consist of around 90 genera, including pepper, tobacco and eggplant. The genus *Lycopersicon* has been divided into two subgenera, the *esculentum* complex which contains those species that can easily be crossed with the commercial tomato and the *peruvianum* complex which contains those species which are crossed with considerable difficulty (Stevens, M., and Rick, C. M. 1986). Due to its value as a crop, *L. esculentum* Miller has become widely disseminated all over the world. Even if the precise origin of the cultivated tomato is still somewhat unclear, it seems to come from the Americas, being native to Ecuador, Peru and the Galapagos Island and initially cultivated by Aztecs and Incas as early as 700 AD. Mexico appears to have been the site of domestication and the source of the earliest introduction.

It is supposed that the cherry tomato, *L. esculentum* var. *cerasiforme*, is the direct ancestor of modern cultivated forms.

Tomato is grown for its fruit, widely used as a fresh market or processed product. As a crop, tomato is grown commercially wherever environmental conditions permit the production of an economically viable yield. The majority of fresh market tomatoes are harvested by hand at vine ripe and mature green stage of ripeness. Fresh market tomatoes are available year round. Processing tomato are mostly mechanically harvested and used in many forms, as canned tomatoes, tomato juice, tomato sauce, puree, paste or even catsup.

Tomato is a normally simple diploid species with twelve pairs of differentiated chromosomes. However, polyploidy tomato is also part of the present invention. The cultivated tomato is self-fertile and almost exclusively self-pollinating. The tomato flowers are hermaphrodites. Commercial cultivars were initially open pollinated. As hybrid vigor has been identified in tomatoes, hybrids are replacing the open pollinated varieties by gaining more and more popularity amongst farmers with better yield and uniformity of plant characteristics. Commercial F1 hybrids can be formed in a number of different ways, including by crossing two parental lines directly (single cross hybrids), by crossing a single cross hybrid with another parental line (three-way or triple cross hybrids), or by crossing two different hybrids (four-way or double cross hybrids). Hybrid commercial F1 tomato seed is produced by hand pollination. Pollen of the male parent is harvested and manually applied to the stigmatic surface of the female inbred. Prior to, and after hand pollination, flowers are covered so that insects do not bring foreign pollen and create a mix or impurity. Flowers are tagged to identify pollinated fruit from which seed will be harvested. Once the parental inbreds that give the best hybrid performance have been identified, the hybrid seed can be reproduced indefinitely as long as the homogeneity of the inbred parents is maintained.

The production of hybrids is a well-developed industry, involving the isolated production of both the parental lines and the hybrids which result from crossing those lines.

Due to its wide dissemination and high value, tomato has been intensively bred. This explains why such a wide array of tomato is now available. The shape may range from small to large, and there are cherry, plum, pear, blocky, round, and beefsteak types. Tomatoes may be grouped by the amount of time it takes for the plants to mature fruit for harvest and, in general the cultivars are considered to be early, midseason or late-maturing. Tomatoes can also be grouped by the plant's growth habit; determinate, semi-determinate or indeterminate. Determinate plants tend to grow their foliage first, then set flowers that mature into fruit if pollination is successful. All of the fruits tend to ripen on a plant at about the same time. Indeterminate tomatoes start out by growing some foliage, then continue to produce foliage and flowers throughout the growing season. These plants will tend to have tomato fruit in different stages of maturity at any given time. The semi-determinate tomatoes have a phenotype between determinate and indeterminate, they are typical determinate types except that grow larger than determinate varieties. More recent developments in tomato breeding have led to a wider array of fruit color. In addition to the standard red ripe color, tomatoes can be creamy white, lime green, pink, yellow, golden, orange or purple.

Hybrid commercial tomato seed can be produced by hand pollination. Pollen of the male parent is harvested and manually applied to the stigmatic surface of the female inbred. Prior to and after hand pollination, flowers are covered so that insects do not bring foreign pollen and create a mix or impurity. Flowers are tagged to identify pollinated fruit from which seed will be harvested Increasing the yield of tomato plants is one of the major goals of tomato plant breeding. For years, plant tomato breeders have used wild species as a reservoir for genes and other genetic sequences for improving cultivated tomato plants.

In 1998, Bernacchi et al. (Bernacchi et al, 1998a) created Near Isogenic Lines developed for 15 genomic regions from the wild donor *L. hirsutum* LA1777, predicted to contain 25 quantitative trait factors for the improvement of seven agronomic traits such as yield, soluble solids, viscosity, fruit color and fruit firmness. Monforte & Tanksley (Monforte & Tanksley, 2000) disclose determinate tomato plants, comprising an introgression fragment from LA1777, allegedly imparting an increased total yield.

In 1995, Eshed and Zamir created introgression lines originating from a cross between the green fruited species *Lycopersicum pennellii* LA716 and the cultivated tomato M82. Each of the created lines contained a single *Lycopersicum pennellii* fragment and together, the lines provided complete coverage of the genome. QTLs for plant weight yield and soluble solids were identified. Among them, a genetic fragment was found at the lower arm of chromosome 1 of the *Lycopersicum pennellii*, which was further demonstrated to increase the yield of determinate processing tomatoes (Eshed and Zamir, 1995, 1996, Bernacchi et al 1998b).

The use of such *Lycopersicum pennellii* or *L. hirsutum* genetic fragment was therefore considered as a straightforward way to increase the yield of tomato plants, whether determinate or indeterminate tomato plants, but, when introgressed into an indeterminate tomato genetic background, the inventors of the present invention have found that the tomato plant bearing these introgressed sequences do not show the expected yield increase (see examples 1 and 4 of the experimental section).

There is thus an important need in the art to identify a source of yield increase for indeterminate tomato plants, which could be used to obtain indeterminate tomato plants showing a yield increase, and a need for improved *S. lycopersicum* plants showing such a yield increase.

The present invention provides commercial *S. lycopersicum* tomato plants that display an increased yield, as well as methods that produce or identify *S. lycopersicum* plants or populations (germplasm) that display such an increased yield. The present invention also discloses molecular genetic markers, especially SNPs, linked to the increased yield loci.

Unexpectedly, the sequences introgressed into the *S. lycopersicum* plants according to the invention provide an increased yield to the indeterminate tomato plants, but also to determinate tomato plants.

Further, it is generally known and well reported that in tomato, there is a negative correlation between the yield, i.e. the total weight of fruits per plants, and the fruit sugar content. The total yield of a plant is affected by both the number of fruit and the size or weight of each fruit; these traits are often referred to as "yield components".

The negative correlation is generally suggested because the increase in yield is limited by the amount of sugars that the plant can allocate into the fruit. This has led to the use of the Brix*Yield (or Brix x Yield) trait (i.e. the multiplication of total weight of fruit on the plant and the fruit sugar content), where this Brix*Yield represents the amount of sugar allocated to fruit by the plant (Eshed and Zamir, 1995).

In addition to the negative correlation between total yield and fruit soluble solid content, a similar negative correlation was described between the yield component of fruit size or weight, and fruit soluble solid content.

Contrary to this teaching, the tomato plants of the present invention do not show such a negative correlation. The plants of the invention indeed exhibit both an increased yield coupled to an increased amount of soluble sugars and solids allocated to fruits (Brix x Yield and TSS x Yield).

DETAILED DESCRIPTION OF THE INVENTION

The present inventors have identified a wild tomato accession of *S. habrochaites* (also known as *L. hirsutum*) HABR1, exhibiting a QTL (quantitative trait locus) which, once introgressed into in the *S. lycopersicum* background, especially on chromosome 1, confer an improved phenotype, cumulating both an increased yield and an increased amount of soluble sugars allocated to fruits (Brix*Yield), with respect to the plant before introgression of said QTL. This wild accession is distinct from the accession LA1777 referred to in Bernacchi et al, 1998a and 1998b and Monforte & Tanksley, 2000. The increases in yield and in Brix*Yield (or Brix x Yield) are also characterized by the absence of a statistically significant decrease in Total Soluble Solids. The improved phenotype is observed in presence of the introgressed sequences, once introgressed into a *S. lycopersicum* genetic background.

The presence in HABR1 of a QTL having these properties is highly unexpected insofar as the wild accession does not have such an improved phenotype, i.e. the sequences or QTL of interest do not confer the improved phenotype in a genetic background which is not *S. lycopersicum* genetic background. Finally, the simultaneous increase of yield and brix*yield is unexpected as not only were yield and brix*yield thought as negatively correlated, but already known QTL modifying these factors were always entirely distinct. They were also negatively impacting the Total Soluble Solids of the plant, contrary to the sequences of the invention.

Finally, the QTL identified by the inventors has the advantageous property of improving the yield and brix*yield of a *S. lycopersicum* plant, once introgressed into its genome, irrespectively of whether the plant is determinate or indeterminate.

The present inventors have thus identified a genetic source conferring an improved phenotype as defined above, which source has never been tested before in this respect. Moreover, they have been able to introgress the *S. habrochaites* sequences responsible for this improved phenotype.

By introgression, it is meant the infiltration of the genes or of genomic sequences of one species into the gene pool of another one from an initial interspecific hybrid between these species.

Regarding the introgressed sequences from the specific *S. habrochaites* accession HABR1 conferring the improved phenotype of interest, they are chosen from those present in the genome of a plant of the tomato seed ToPATYIELD. A sample of this *S. lycopersicum* seed has been deposited by Hazera Seeds Ltd, Berurim, M. P. Shikmim 79837, Israel, pursuant to, and in satisfaction of, the requirements of the Budapest Treaty on the International Recognition of the Deposit of Microorganisms for the Purposes of Patent Procedure (the "Budapest treaty") with the National Collection of Industrial, Food and Marine Bacteria (NCIMB), (NCIMB Ltd, Ferguson Building, Craibstone Estate, Bucksburn, Aberdeen AB21 9YA, United Kingdom), on 4 Apr. 2016, under accession number NCIMB 42567.

A deposit of this tomato seed is maintained by Hazera Seeds Ltd, Berurim, M. P. Shikmim 79837, Israel.

The deposited seeds, and plants thereof, have been obtained from an initial interspecific cross between a plant of *S. habrochaites*, i.e. the introgression partner HABR1 displaying the QTL of interest, but not the phenotype of interest, and a plant of the line *S. lycopersicum* Moneyberg, the recurrent parent, followed by several backcrosses. The deposited seeds are from a line, comprising introgressed sequences from *S. habrochaites* only on chromosome 1. The deposited seeds represent a reservoir of introgressed sequences from *S. habrochaites* in the *S. lycopersicum* genome. The introgressed sequences conferring the improved phenotype according to the invention, i.e. a combined increased yield and increased Brix x yield, are chosen from this reservoir, especially on chromosome 1.

According to a first aspect, the present invention is thus directed to a *Solanum lycopersicum* plant comprising in its genome, introgressed sequences from *S. habrochaites*, which confer to the plant an improved phenotype with respect to a corresponding *S. lycopersicum* plant devoid of said sequences. The improved phenotype according to the present invention corresponds to the combination of an increased yield and an increased amount of soluble sugars allocated to fruits (Brix*Yield or Brix x Yield), with respect to a corresponding *S. lycopersicum* plant devoid of said introgressed sequences. The invention is also directed to a cell of such a plant and seed, comprising these introgressed sequences. The introgressed sequences, or QTL, confer the phenotype irrespective of the growth habit of the *S. lycopersicum* plant, i.e. either determinate, semi-determinate or indeterminate.

By Yield it to be understood to the total fruit yield per plant, especially the total marketable fruit yield per plant, including the red and green fruit. This parameter is measured over the whole life of the plants, irrespective of its determinate or indeterminate growth habit.

By Brix*Yield (or Brix x yield) is to be understood as the weight of soluble sugars produced per plant, Brix referring to the soluble sugars, and especially sucrose in the fruits. The higher the brix (or brix degree), the more sugar content. The brix measurement is important to assess fruit taste as fruits with low brix and therefore poor sugar content will not be appreciated by customers. TSS (Total Soluble Solids) refers to all sugars as well as organic acids in the fruits.

Brix degree and TSS (Total Soluble Solids) are highly correlated parameters such that increase in Brix*Yield and increase in TSS*Yield are concomitant; the increase in one or the other of these parameters is thus used interchangeably in the following. Insofar as the term Brix*Yield is widely used and commonly accepted by professionals in the field of the invention, this term is however preferably used in the following description. It is however to be understood that the plants, cells and seeds of the invention can be equally characterized by an increased Brix*Yield (Brix x Yield) or an increased TSS*Yield (TSS x Yield).

By an "increased yield" or an "increased Brix*Yield", it is to be understood an increase which is statistically significant.

Whereas the improved phenotype is characterized by the simultaneous increases of the yield and Brix*Yield, or Yield and TSS*Yield; for a plant of the invention having the introgressed sequences, the increase in yield and the increase in Brix*Yield, and thus in TSS*Yield, may however be distinct, of different magnitude.

The increase is preferably an increase of at least 10% for both parameters, and preferably at least 15% for both parameters, even preferably at least 20% for both parameters. The increase may also be an increase of at least 20% for at least one of the parameters, and at least 10% or at least 15% for the other. As detailed above, the increase is evaluated with respect to a corresponding plant which is distinct from a plant of the invention only by the absence of the introgressed sequences from *S. habrochaites* and presence of the corresponding sequences of *S. lycopersicum*.

The increased yield and increased TSS*Yield or Brix*Yield can be measured inter alia in greenhouses, for example as detailed in the example section. The increase in these parameters can be observed irrespective of the growing season, when there are more than one growing season per year like in Israel, and irrespective of the location.

The introgressed sequences according to the invention, conferring the improved phenotype as disclosed above are introgressed sequences chosen from those present in the genome of seeds of ToPATYIELD corresponding to NCIMB accession number 42567.

Whereas all deposited seeds possess an introgressed fragment at the same locus on both homologues of chromosome 1, and conferring the phenotype according to the invention, this introgressed fragment may slightly vary in length between the seeds.

As used herein, homologous chromosomes, or homologs (or homologues), refer to a set of one maternal and one paternal chromosomes that pair up with each other during meiosis. These copies have the same genes in the same loci and the same centromere location.

The introgressed sequences are preferably to be found on chromosome 1 of a *S. lycopersicum* plant of the invention.

The introgressed sequences act as a single dominant allele of a gene responsible for the improved phenotype i.e. the trait is monogenic and dominant. Plants homozygous and heterozygous for the introgressed sequences both fully exhibit the improved phenotype as defined above.

The introgressed sequences of the invention, conferring the phenotype in *S. lycopersicum* background, thus constitute Quantitative Trait Loci (QTL) underlying the trait corresponding to the improved phenotype, namely a single QTL responsible for both the increased yield and the increased Brix*Yield.

The introgressed sequences conferring the improved phenotype of the invention are more preferably located within a chromosomal interval of chromosome 1 which comprises the SNP SL10332_112 (SEQ ID No. 1) and the SNP EE_2225 (SEQ ID No. 13), more preferably within the chromosomal region delimited by, and preferably comprising, SNP SL10332_112 and SNP EE_2225.

The specific polymorphisms corresponding to the SNPs (Single Nucleotide Polymorphism) referred to in this description, as well as the flanking sequences of these SNPs in the *S. lycopersicum* genome, are given in the experimental section (see inter alia table 2) and accompanying sequence listing. Their location with respect to the version 2.5 of the tomato genome, on chromosome 1, is indicated in table 2, and their flanking sequences are also illustrated in table 2 and in the sequence listing.

It is to be noted in this respect that, by definition, a SNP refers to a single nucleotide in the genome, which is variable depending on the allele which is present, whereas the flanking nucleotides are identical. For ease of clear identification of the position of the different SNPs, their position is given in table 2, by reference to the tomato genome sequence and by reference to their flanking sequences, identified by SEQ ID number. In the sequence associated with a specific SNP in the present application, for example SEQ ID No:1 for the SNP SL10332_112, only one nucleotide within the sequence actually corresponds to the polymorphism, namely the $61^{st}$ nucleotide of SEQ ID No:1 corresponds to the polymorphic position SNP SL10332_112, which can be C or T as indicated in tables 1 and 2. The flanking sequences are given for positioning the SNP in the genome but are not part of the polymorphism as such.

The present inventors have identified that introgressed sequences essential for the phenotype of interest are to be found in the chromosomal region mentioned above, by identifying the presence of introgressed sequences at different loci along said region, namely at 13 different loci defined by the 13 following SNPs: SL10332_112, EP_1592, EP_1027, EP_1150, EP_1876, EE_4621, SL10522_138, EP_0051, IL2_3605, SL20213_779, SL20071_190, IL2_6411 and EE_2225. The presence of introgressed sequences from S. habrochaites at these loci is thus indicative of the improved phenotype of the invention. These 13 SNPs are referred to herewith as the 13 SNPs of the invention.

Therefore, according to another embodiment of the invention, the introgressed sequences present in the genome of a plant, seed or cell of the invention are preferably to be found at least at one or more of the 13 loci encompassing said 13 SNPs mentioned above, namely the locus encompassing SL10332_112 (SEQ ID No. 1), the locus encompassing EP_1592 (SEQ ID No. 2), the locus encompassing EP_1027 (SEQ ID No. 3), the locus encompassing EP_1150 (SEQ ID No. 4), the locus encompassing EP_1876 (SEQ ID No. 5), the locus encompassing EE_4621 (SEQ ID No. 6), the locus encompassing SL10522_138 (SEQ ID No. 7), the locus encompassing EP_0051 (SEQ ID No. 8), the locus encompassing IL2_3605 (SEQ ID No. 9), the locus encompassing SL20213_779 (SEQ ID No. 10), the locus encompassing SL20071_190 (SEQ ID No. 11), the locus encompassing IL2_6411 (SEQ ID No. 12) and/or the locus encompassing EE_2225 (SEQ ID No. 13), for example at 2, 3, 4, 8, 10 or 12 of these 13 loci, or at all of them.

It is to be noted that, when introgressed sequences are to be found at more than one of the preceding loci, they are preferably to be found on the same homologue of chromosome 1, irrespective of the ploidy of the plant, seed or cell.

When the introgressed sequences from S. habrochaites conferring the improved phenotype of the invention are found in a locus encompassing a given SNP, this means that the allele of this SNP is the allele found in the wild S. habrochaites introgression partner HABR1 and also in the deposited seeds ToPATYIELD (NCIMB 42567). This also means that the 5' flanking region of said SNPs, or the 3' flanking region of said SNP, or both regions, are also identical to S. habrochaites sequences in this region. Therefore, this given SNP may form part of the 3' border or 5' border of the introgressed interval, or may be within the introgressed interval conferring the desired phenotype.

The alleles of the 13 SNPs of the invention corresponding to the alleles of the S. habrochaites partner conferring the improved phenotype, are: allele T of SL10332_112, allele C of EP_1592, allele C of EP_1027, allele G of EP_1150, allele G of EP_1876, allele A of EE_4621, allele G of SL10522_138, allele T of EP_0051, allele T of IL2_3605, allele G of SL20213_779, allele C of SL20071_190, allele A of IL2_6411 and allele T of EE_2225. The presence of the introgressed sequences of interest can be revealed by the presence of said specific alleles, characteristic or representative of the introgression partner conferring the improved phenotype, and distinct from the allele of the recurrent S. lycopersicum parent for these SNPs. The alleles of these SNPs can thus reflect the presence of the introgression sequences of the invention.

The presence of introgressed sequences into the genome of a S. lycopersicum plant, seed or cell may for example be shown by GISH (genetic in situ hybridization). GISH is indeed a powerful technique for detection of the introgression of chromatin material from one species onto another species. The advantage of GISH is that the introgression process is visualized by means of 'pictures of the introgressed genome'. With this technique, it is also possible to establish whether a particular region of the genome is homozygous or heterozygous, thanks to the use of molecular cytogenetic markers which are co-dominant. By this technique, it is also possible to determine in which chromosome and chromosome homologue an introgressed gene of interest is present.

Preferably, in the genome of a S. lycopersicum plant of the invention, excepted the introgressed sequences on chromosome 1, conferring the phenotype of interest and chosen from those present in ToPATYIELD seeds NCIMB accession number 42567, there are no other introgressed interval of 5 kilobases or more in length, from S. habrochaites, preferably no other introgressed interval of 1 kb or more from S. habrochaites. It is however not excluded that other introgressed sequences, from other wild accessions, are to be found in the genome of a plant of the invention.

According to a most preferred embodiment, the introgressed sequences conferring the phenotype correspond to a single introgressed interval on chromosome 1. According to this embodiment, the chromosomal interval conferring the phenotype of interest, especially the interval or region delimited on one side by SL10332_112 and on the other side by EE_2225, exclusively comprises or corresponds to introgressed sequences from S. habrochaites. According to this embodiment, in a plant, seed or cell of the invention, the genomic fragment corresponding to said interval, is an introgression fragment from S. habrochaites and therefore has the same sequence as the genomic fragment delimited by the same SNPs in the deposited seeds ToPATYIELD NCIMB 42567.

It is noted in this respect that specific positions in a chromosome can indeed be defined with respect to single nucleotide polymorphism, insofar as the flanking sequences of said SNPs are defined in order to unambiguously position them on the genome. The present inventors have used SNPs, identified by their flanking sequences, present in the S. habrochaites and in S. lycopersicum genomes with different alleles, to discriminate between introgressed and endogenously residing sequences and to track down the introgressed sequences from S. habrochaites in S. lycopersicum genome.

A chromosomal region delimited by two SNPs X and Y refers to the section of the chromosome lying between the positions of these two SNPs and comprising said SNPs, therefore the nucleotide sequence of this chromosomal region begins with the nucleotide corresponding to SNP X and ends with the nucleotide corresponding to SNP Y, i.e. the SNPs are comprised within the region they delimit, in the sense of the invention.

According to a preferred embodiment, the introgressed sequences from S. habrochaites in a plant, seed or cell of the invention, especially an introgressed interval as defined above, comprises at least 10 kilobases, preferably at least 100 kilobases, at least 1000 kilobases.

In a plant, seed or cell of the invention, the presence of the introgressed sequences conferring the phenotype of interest is preferably characterized by SNPs IL2_3605 and/or IL2_6411, more specifically by allele T of IL2_3605 and/or by allele A of IL2_6411, and preferably by the presence of both alleles simultaneously on one homologue of chromosome 1, or on both, of a plant, seed or cell of the invention.

The introgressed sequences from S. habrochaites conferring the improved phenotype of the invention are to be found homozygously or heterozygously in a plant, seed or cell of the invention.

According to still another embodiment, a plant of the invention is a determinate, indeterminate or semi-indeterminate plant, or seed or cell thereof, i.e. corresponding to determinate indeterminate or semi-indeterminate growth habit.

By determinate, it is meant tomato plants which tend to grow their foliage first, then set flowers that mature into fruit if pollination is successful. All of the fruits tend to ripen on a plant at about the same time. Indeterminate tomatoes start out by growing some foliage, then continue to produce foliage and flowers throughout the growing season. These plants will tend to have tomato fruit in different stages of maturity at any given time. The semi-determinate tomatoes have a phenotype between determinate and indeterminate, they are typical determinate types except that grow larger than determinate varieties.

The invention is also directed to hybrid plants of S. lycopersicum, obtainable by crossing a plant having the improved phenotype and bearing homozygously the introgressed sequences of the invention, with another S. lycopersicum, preferably with a plant devoid of S. habrochaites introgression sequences.

Preferably, a S. lycopersicum plant according to the invention is a commercial plant or line. Such a commercial plant or line preferably also exhibits resistance to ToMV (tomato mosaic virus), for example due to the presence of a Tm-2 (allele Tm-2 or Tm-$2^2$ (also known as Tm-$2^a$)) or Tm-1 resistance gene, which also confers resistance to TMV (Tobacco Mosaic Virus). A plant according to this aspect of the invention preferably has also the following additional features: nematode resistance trait (Mi-1 or Mi-j), as well as Fusarium and Verticillium resistances.

Moreover, the commercial plant of the invention gives rise to fruits in suitable conditions, which are at least 10 grams at full maturity, preferably at least 25 g at full maturity and or even more preferred at least 50 g at full maturity.

As detailed above, the invention is directed to S. lycopersicum plants, exhibiting the improved phenotype, as well as to seeds giving rise to those plants.

A plant or seed according to the invention may be a progeny or offspring of a plant grown from the deposited seeds ToPATYIELD, deposited at the NCIMB under the accession number NCIMB 42567. Plants grown from the deposited seeds are indeed homozygous for the introgressed sequences conferring the improved phenotype, they thus bear in their genome the introgressed sequences of interest on each of the homologues of chromosome 1. They can be used to transfer these sequences into another background by crossing and selfing and/or backcrossing.

The invention is also directed to the deposited seeds of ToPATYIELD (NCIMB 42567) and to plants grown from one of these seeds. These seeds contain homozygously the introgressed sequences conferring the phenotype of interest; they are however distinct on some other phenotypic traits such that they do not form a plant variety.

The invention is also directed to plants or seeds as defined above, i.e. containing the introgressed sequences of interest in homozygous or heterozygous state, said sequences conferring the improved phenotype, which plants or seeds are obtainable by transferring the introgressed sequences from a S. lycopersicum plant, representative seeds thereof were deposited under NCIMB accession NCIMB-42567, into another S. lycopersicum genetic background, for example by crossing said plant with a second tomato plant parent and selection of the plant bearing the introgressed sequences responsible for the phenotype of interest.

The invention in a second aspect also concerns any plant likely to be obtained from seed or plants of the invention as described above, and also plant parts of such a plant, and most preferably explant, scion, cutting, seed, fruit, root, rootstock, pollen, ovule, embryo, protoplast, leaf, anther, stem, petiole, and any other plants part, wherein said plant, explant, scion, cutting, seed, fruit, root, rootstock, pollen, ovule, embryo, protoplast, leaf, anther, stem, petiole, and/or plant part is obtainable from a seed or plant according to the first aspect of the invention, i.e. bearing the introgressed sequences of interest homozygously or heterozygously in their genome. These plant parts, inter alia explant, scion, cutting, seed, fruit, root, rootstock, pollen, ovule, embryo, protoplast, leaf, anther, stem or petiole, comprise in their genome the introgressed sequences from S. habrochaites conferring the phenotype of interest, i.e. increased yield and increased brix*yield or increased yield and increased TSS*yield. The introgressed sequences referred to in this aspect of the invention are those defined above in the context of plants of the invention. The different features of the introgressed sequences defined in relation with the first aspect of the invention apply mutatis mutandis to this aspect of the invention. The introgressed sequences are thus preferably chosen from those present in the genome of a plant corresponding to the deposited material ToPATYIELD (NCIMB accession number 42567). They are advantageously characterized by the presence of allele T of IL2_3605 and/or allele A of IL2_6411, and preferably by the presence of both alleles simultaneously on one chromosome, namely on at least one homologue of chromosome 1.

The invention is also directed to cells of S. lycopersicum plants, such that these cells comprise, in their genome, introgressed sequences from S. habrochaites conferring the phenotype of interest to a S. lycopersicum plant. The introgressed sequences are those already defined in the frame of the present invention, they are characterized by the same features and preferred embodiments already disclosed with respect to the plants and seeds according to the preceding aspects of the invention. The presence of these introgressed sequences can be revealed by the techniques disclosed above and well known to the skilled reader. It can inter alia be determined whether the introgressed sequences are present homozygously or heterozygously in the genome of such a cell of the invention. They are advantageously characterized by the presence of allele T of IL2_3605 and/or by allele A of IL2_6411, and preferably by the presence of both alleles simultaneously on the same chromosome, namely on at least one homologue of chromosome 1.

Cells according to the invention can be any type of S. lycopersicum cell, inter alia an isolated cell and/or a cell capable of regenerating a whole S. lycopersicum plant, bearing introgressed sequences from S. habrochaites linked to the phenotype of interest.

The present invention is also directed to a tissue culture of regenerable cells of the plant as defined above according to the present invention; preferably, the regenerable cells are derived from embryos, protoplasts, meristematic cells, callus, pollen, leaves, anthers, stems, petioles, roots, root tips, fruits, seeds, flowers, cotyledons, and/or hypocotyls of the invention, and thus contain in their genome introgressed sequences from S. habrochaites on chromosome 1 conferring the improved phenotype, namely increased yield and increased brix*yield/TSS*Yield with respect to a plant devoid of said introgressed sequences.

The tissue culture will preferably be capable of regenerating plants having the physiological and morphological characteristics of the foregoing tomato plant, and of regenerating plants having substantially the same genotype as the foregoing tomato plant. The present invention also provides tomato plants regenerated from the tissue cultures of the invention.

The invention also provides a protoplast of the plant defined above, or from the tissue culture defined above, said protoplast containing the introgressed sequences from *S. habrochaites* conferring the improved phenotype of the invention.

According to another aspect, the present invention is also directed to the use of a tomato plant of the invention, preferably comprising homozygously the introgressed sequences, as a breeding partner in a breeding program for obtaining *S. lycopersicum* plants having the improved phenotype of the invention. Indeed, such a breeding partner harbors homozygously in its genome introgressed sequences from *S. habrochaites*, conferring the phenotype of interest. By crossing this plant with a tomato plant, especially a line, it is thus possible to transfer these sequences, conferring the desired phenotype, to the progeny as the phenotype is a monogenic trait. A plant according to the invention can thus be used as a breeding partner for introgressing sequences conferring the desired phenotype into a *S. lycopersicum* plant or germplasm, inter alia in a breeding program for increasing simultaneously the yield and the amount of soluble sugars allocated to fruits (Brix*Yield) of *S. lycopersicum* plants. Although a plant or seed bearing the introgressed sequences of interest heterozygously, can also be used as a breeding partner as detailed above, the segregation of the phenotype is likely to render the breeding program more complex.

The introgressed sequences from *S. habrochaites* will advantageously be introduced into varieties that contain other desirable genetic traits such as resistance to disease, early fruit maturation, drought tolerance, fruit shape, and the like.

The invention is also directed to the same use with plants or seed of ToPATYIELD, deposited at the NCIMB under the accession number NCIMB 42567. Said plants are also suitable as introgression partners in a breeding program aiming at conferring the desired phenotype to a *S. lycopersicum* plant or germplasm.

In such a breeding program, the selection of the progeny displaying the desired phenotype, or bearing sequences linked to the desired phenotype, can advantageously be carried out on the basis of the alleles of the SNP markers, especially the SNP markers of the invention. The progeny is preferably selected on the presence of allele T of IL2_3605 and/or allele A of IL2_6411, and preferably by the presence of both alleles simultaneously on one homologue of chromosome 1.

The selection can alternatively be made on the basis of the presence of any one of the alleles of the 13 SNPs of the invention linked to the improved phenotype; or a combination of these alleles. According to such an embodiment, the selection can be made on the simultaneous presence of at least 3, 4 or at least 5 of the following SNP alleles: allele T of SNP SL10332_112 (SEQ ID No. 1), allele C of SNP EP_1592 (SEQ ID No. 2), allele C of SNP EP_1027 (SEQ ID No. 3), allele G of SNP EP_1150 (SEQ ID No. 4), allele G of SNP EP_1876 (SEQ ID No. 5), allele A of SNP EE_4621 (SEQ ID No. 6), allele G of SNP SL10522_138 (SEQ ID No. 7), allele T of SNP EP_0051 (SEQ ID No. 8), allele T of SNP IL2_3605 (SEQ ID No. 9), allele G of SNP SL20213_779 (SEQ ID No. 10), allele C of SNP SL20071_190 (SEQ ID No. 11), allele A of SNP IL2_6411 (SEQ ID No. 12) and allele T of SNP EE_2225 (SEQ ID No. 13), in a genetic material sample of the plant to be selected.

The presence of these alleles indeed confirms the presence of introgressed sequences at the loci defined by said SNPs. Moreover, further to point mutation or recombination event, it is conceivable that at least 1 or 2 of these alleles is lost, the remaining of the introgression fragment however still conferring the phenotype of interest.

A plant according to the invention, or grown from a seed as deposited under accession number NCIMB 42567, is thus particularly valuable in a marker assisted selection for obtaining commercial tomato lines and varieties, having the improved phenotype of the invention.

The invention is also directed to the use of said plants in a program aiming at identifying, sequencing and/or cloning the genes conferring the desired phenotype.

Any specific embodiment described for the previous aspects of the invention is also applicable to this aspect of the invention, especially with regard to the features of the introgressed sequences from *S. habrochaites* conferring the phenotype of interest.

The invention is also directed to a method for detecting and/or selecting *S. lycopersicum* plants having introgressed sequences from *S. habrochaites* as found in the genome of the seeds of ToPATYIELD (NCIMB accession number 42567), said introgressed sequences conferring an improved phenotype, corresponding to both an increased yield and an increased amount of soluble sugars allocated to fruits (Brix*Yield), with respect to a corresponding plant devoid of said sequences, the method comprising the detection of at least one of the following markers: allele T of SNP SL10332_112 (SEQ ID No. 1), allele C of SNP EP_1592 (SEQ ID No. 2), allele C of SNP EP_1027 (SEQ ID No. 3), allele G of SNP EP_1150 (SEQ ID No. 4), allele G of SNP EP_1876 (SEQ ID No. 5), allele A of SNP EE_4621 (SEQ ID No. 6), allele G of SNP SL10522_138 (SEQ ID No. 7), allele T of SNP EP_0051 (SEQ ID No. 8), allele T of SNP IL2_3605 (SEQ ID No. 9), allele G of SNP SL20213_779 (SEQ ID No. 10), allele C of SNP SL20071_190 (SEQ ID No. 11), allele A of SNP IL2_6411 (SEQ ID No. 12) and allele T of SNP EE_2225 (SEQ ID No. 13), in a genetic material sample of the plant to be selected.

According to a still another aspect, the invention also concerns methods or processes for the production of *S. lycopersicum* plants having the desired phenotype, especially commercial plants and inbred parental lines. The present invention is indeed also directed to transferring the introgressed sequences conferring the improved phenotype as defined, to other tomato varieties, or other species or inbred parental lines, and is useful for producing new types and varieties of tomatoes.

A method or process for the production of a plant having these features may comprise the following steps:

a) Crossing a plant grown from a deposited seed NCIMB 42567, or progeny thereof, bearing the sequences conferring both an increased yield and an increased amount of soluble sugars allocated to fruits (Brix*Yield) with respect to a corresponding plant devoid of said sequences, and an initial *S. lycopersicum* plant, preferably devoid of said sequences;

b) Selecting one plant in the progeny thus obtained, having both an increased yield and an increased amount of soluble sugars allocated to fruits (Brix*Yield), with respect to the initial plant;

c) Optionally self-pollinating one or several times the plant obtained at step b) and selecting in the progeny thus obtained a plant having both an increased yield and an increased amount of soluble sugars allocated to fruits (Brix*Yield), with respect to the initial plant.

Alternatively, the method or process may comprise instead of step a) the following steps:
- a1) Crossing a plant corresponding to the deposited seeds (NCIMB 42567), or progeny thereof bearing the sequences conferring both an increased yield and an increased amount of soluble sugars allocated to fruits (Brix*Yield) with respect to a corresponding plant devoid of said sequences, and an initial *S. lycopersicum* plant, preferably devoid of said sequences,
- a2) Increasing the F1 hybrid by means of selfing to create F2 population.

In the above methods or processes, SNPs markers are preferably used in steps b) and/or c), for selecting plants bearing sequences conferring the phenotype of interest, i.e. increased brix*yield and increased yield.

The SNP markers are preferably one or more of the 13 SNP markers of the invention, and preferably one or both of the 2 preferred SNP markers IL2_3605 and IL2_6411.

According to a preferred embodiment, the selection is at least partly made on the basis of the allele of IL2_3605 and/or by the allele of IL2_6411. The selection is even more preferably carried out by detecting the alleles of these 2 SNP markers. Alternatively, the selection can be made on the detection of the allele of at least 2 SNPs chosen amongst the 13 SNPs of the invention.

Preferably, the selection is made on at least 3 SNPs, preferably at least 4, 5 or 6, at least one or two of them being IL2_3605 and/or IL2_6411. The selection can also be made on the detection of the alleles of all these SNPs.

According to a preferred embodiment, the selection is made on the basis of the alleles of the 2 SNPs IL2_3605 and IL2_6411.

By selecting a plant on the basis of the allele of one or more SNPs, it is to be understood that the plant is selected as having both an increased yield and an increased amount of soluble sugars or solids allocated to fruits (Brix*Yield or TSS*Yield), with respect to the initial plant, when the allele of the SNP(s) is (are) the allele corresponding to the allele of the HABR1 parent for this SNP and not the allele of the initial *S. lycopersicum* plant. For example, a plant can be selected as having the improved phenotype of the invention, when allele T of SNP IL2_3605 and/or allele A of SNP IL2_6411 is detected.

Preferably, the *S. lycopersicum* plant of step a) is an elite line, used in order to obtain a plant with commercially desired traits or desired horticultural traits.

A method or process as defined above may advantageously comprises backcrossing steps, preferably after step c), in order to obtain plants having all the characterizing features of *S. lycopersicum* plants. Consequently, a method or process for the production of a plant having these features may also comprise the following additional steps:
- d) Backcrossing the plant selected in step b) or c) with a *S. lycopersicum* plant;
- e) Selecting a plant having both an increased yield and an increased amount of soluble sugars allocated to fruit (Brix*Yield), with respect to the initial plant.

The plant used in step a), namely the plant corresponding to the deposited seeds can be a plant grown from the deposited seeds; it may alternatively be any plant according to the 1$^{st}$ aspect of the invention, bearing the introgressed sequences conferring the phenotype, preferably bearing these sequences homozygously.

At step e), SNPs markers can be used for selecting plants having both an increased yield and an increased amount of soluble solids and sugars allocated to fruit (TSS*Yield and Brix*Yield), with respect to the initial plant. The SNP markers are those of the invention, as described in the previous sections.

According to a preferred embodiment, the method or process of the invention is carried out such that, for at least one of the selection steps, namely b), c) and/or e), the selection is based on the detection of at least one of the following alleles: allele T of SNP SL10332_112, allele C of SNP EP_1592, allele C of SNP EP_1027, allele G of SNP EP_1150, allele G of SNP EP_1876, allele A of SNP EE_4621, allele G of SNP SL10522_138, allele T of SNP EP_0051, allele T of SNP IL2_3605, allele G of SNP SL20213_779, allele C of SNP SL20071_190, allele A of SNP IL2_6411 and allele T of SNP EE_2225.

When the selection is made on the basis of more than one SNPs, it is preferred that the selection is based on the presence, on the same homologue of the chromosome 1, of the alleles representative of the HABR1 parent.

Preferably, the selection is based on the simultaneous presence of allele T of SNP IL2_3605 and allele A of SNP IL2_6411, especially the simultaneous presence of both alleles on the same homologue of chromosome 1.

It is to be noted that, when plants having the improved phenotype, and bearing homozygously the introgressed sequences conferring this phenotype, are to be selected, the selection is to be made on the basis of one or more the SNPs of the invention, on the presence of the alleles representative of the introgressed sequences, namely the alleles of the HABR1 parent, coupled to the absence of the alleles representative of the recurrent *S. lycopersicum* parent.

Preferably, each selection step is carried out by detection of allele T of SNP IL2_3605 and allele A of SNP IL2_6411, on the same homologue of chromosome 1.

The plant selected at step e) is preferably a commercial plant, especially a plant having fruits which weigh at least 25 g, or at least 50 g at full maturity in normal culture conditions.

Preferably, steps d) and e) are repeated at least twice and preferably three times, not necessarily with the same *S. lycopersicum* plant. Said *S. lycopersicum* plant is preferably a breeding line.

Resistance to nematode trait or resistance to ToMV may additionally be selected, at each selection step of the processes disclosed above.

The self-pollination and backcrossing steps may be carried out in any order and can be intercalated, for example a backcross can be carried out before and after one or several self-pollinations, and self-pollinations can be envisaged before and after one or several backcrosses.

The selection of the progeny having the desired improved phenotype can also be made on the basis of the comparison of Yield and Brix*Yield with Yield and Brix*Yield the *S. lycopersicum* parent, as disclosed inter alia in the examples.

The method used for allele detection can be based on any technique allowing the distinction between two different alleles of a SNP, on a specific chromosome.

The plant selected at the end of the process, at step c) or e) or after any further steps as disclosed above, is advantageously a parental inbred tomato line which can be used for production of hybrid commercial F1 tomato seeds, by crossing said parental line, homozygous for the introgressed sequences of the invention, with another inbred line, preferably not bearing said sequences. The plants grown from the seeds thus obtained have the improved phenotype according to the invention.

The invention is also directed to a method or process for obtaining *S. lycopersicum* plants having the desired improved phenotype, wherein said method comprises the steps of:
- a) Making an interspecific cross between a *S. habrochaites* plant and a *S. lycopersicum* plant, b) Selecting one hybrid in the progeny thus obtained bearing the sequences linked to the improved phenotype,
- c) self-pollinating one or several times the plant obtained at step b) and selecting a hybrid in the progeny thus obtained bearing the sequences linked to the improved phenotype;
- d) backcrossing the hybrid selected in step b) or c) with a *S. lycopersicum* plant;
- e) selecting a plant bearing the introgressed sequence conferring the improved phenotype,
- f) Optionally self-pollinating the plant obtained at step e), and
- g) Optionally selecting a plant bearing the introgressed sequence conferring the improved phenotype, wherein steps d) to g) can be repeated and wherein SNPs markers are used in steps b), c), e) and/or g) for selecting plants having the improved phenotype, corresponding to increased yield coupled to increased Brix*Yield, as detailed for the previous methods.

The plant selected at the end of the method is preferably a commercial plant or an inbred parental line thereof, especially a plant having fruits which weigh at least 25 g, or at least 50 g, at full maturity in normal culture conditions.

The invention also concerns a method wherein steps a) to c) are not carried out and wherein step d) is carried out with a plant obtained from the deposited seed (NCIMB accession number 42567) instead of the hybrid mentioned above in step d).

All preferred embodiments recited above for the previous method apply mutatis mutandis to this alternative method. Especially, steps d) and e) can be repeated, they are preferably carried out twice, or three times. The same applies to steps f) and g) which are preferably carried out twice, three times or more. The plant thus obtained is preferably for use as a parental inbred line for the production of hybrid commercial F1 tomato seeds.

The present invention also concerns a plant obtained or obtainable by such a method. Such a plant is indeed a *S. lycopersicum* plant having the improved phenotype according to the first aspect of the invention.

The invention is also directed to a method for obtaining commercial tomato plants or inbred parental lines thereof, having the desired improved phenotype, corresponding to both an increased yield and an increased amount of soluble sugars and solids allocated to fruit (Brix*Yield), with respect to an initial commercial *S. lycopersicum* plant, comprising the steps of:
- a) Backcrossing a plant obtained by germinating a deposited seed ToPATYIELD NCIMB accession number 42567, with a commercial *S. lycopersicum* plant,
- b) Selecting a plant having the improved phenotype.

Preferably, the selection is made on the basis of one or more of the 13 SNPs of the invention, as detailed for the other methods of the invention.

According to a preferred embodiment, step b) is a step of selecting a plant bearing allele T of SNP IL2_3605 and allele A of SNP IL2_6411, preferably on the same homologue of chromosome 1.

In all the methods and processes of the invention according to the invention, the initial *S. lycopersicum* plant is determinate, indeterminate or semi-determinate. According to a preferred embodiment of the invention, the *S. lycopersicum* plant used in the processes is a plant having an indeterminate growth habit.

As already disclosed, the tomato plants according to the invention are preferably also resistant to Tomato Mosaic Virus, to nematodes, and to *Fusarium* and *Verticillium*. In order to obtain such plants in the processes and methods of the invention, the *S. lycopersicum* parents used in the breeding schemes are preferably bearing sequences conferring resistance to Tomato Mosaic Virus, to nematodes, and to *Fusarium* and *Verticillium*; and the selection steps are carried out to select plants having these resistance sequences, in addition to the introgressed sequences conferring the improved phenotype of the invention.

The present invention is also directed to a *S. lycopersicum* plant obtainable by any of the methods and processes disclosed above.

In addition to introgression of the sequences conferring the improved phenotype as detailed in the methods of the invention, said sequences can also be introduced into *S. lycopersicum* background by genetic engineering in order to obtain a commercial *S. lycopersicum* plant exhibiting the improved phenotype. The identification and cloning of the introgressed sequences from *S. habrochaites* conferring the desired phenotype, inter alia from the deposit, are routine for the skilled person.

The invention is moreover directed to a method for detecting and/or selecting *S. lycopersicum* plants having introgressed sequences from *S. habrochaites* conferring the improved phenotype, on the basis of the allele detection of at least one SNP chosen amongst the 13 SNPs of the invention on chromosome 1, preferably at least SNP IL2_3605 and IL2_6411.

Preferably, plants bearing the introgressed sequences are selected if at least one of the following markers, and preferably at least 2, 3, 4, 5 or all, of allele T of SNP SL10332_112, allele C of SNP EP_1592, allele C of SNP EP_1027, allele G of SNP EP_1150, allele G of SNP EP_1876, allele A of SNP EE_4621, allele G of SNP SL10522_138, allele T of SNP EP_0051, allele T of SNP IL2_3605, allele G of SNP SL20213_779, allele C of SNP SL20071_190, allele A of SNP IL2_6411 and allele T of SNP EE_2225, is/are detected, in a genetic material sample of the plant to be selected, preferably on the same homologue of chromosome 1. More preferably, a plant is selected if at least one or both the following alleles is/are detected: allele T of SNP IL2_3605 and allele A of SNP IL2_6411, preferably on the same homologue of chromosome 1.

The invention is also directed to the use of the information provided herewith by the present inventors, namely the existence of a QTL, present in HABR1 and in the deposited seeds, and conferring the improved phenotype to *S. lycopersicum* plants, and the disclosure of molecular markers associated to this QTL. This knowledge can be used inter alia for precisely mapping the QTL, for defining its sequence, for identifying tomato plants comprising the QTL conferring the improved phenotype and for identifying further or alternative markers associated to this QTL. Such further markers are characterized by their location, namely close to the markers disclosed in the present invention, and by their association with the phenotype of interest, revealed by the invention.

The invention thus concerns the use of one or more molecular markers, for fine-mapping or identifying a QTL, or introgressed sequences, in the tomato genome, said QTL or introgressed sequences conferring the improved phenotype of the invention to *S. lycopersicum* plants, wherein said one or more markers is/are localized in the chromosomal region delimited on chromosome 1 by the SNP markers SL10332_112 and EE_2225, or at less than 1 megabase unit from the locus of one of the 13 SNP markers of the invention, namely at less than 1 megabase from the locus of one of the SNP markers SL10332_112, EP_1592, EP_1027, EP_1150, EP_1876, EE_4621, SL10522_138, EP_0051, IL2_3605, SL20213_779, SL20071_190, IL2_6411 and EE_2225. Said one or more molecular marker(s) is/are moreover preferably associated, with a p-value of 0.05 or less, with at least one of the following SNP alleles: allele T of SNP SL10332_112, allele C of SNP EP_1592, allele C of SNP EP_1027, allele G of SNP EP_1150, allele G of SNP EP_1876, allele A of SNP EE_4621, allele G of SNP SL10522_138, allele T of SNP EP_0051, allele T of SNP IL2_3605, allele G of SNP SL20213_779, allele C of SNP SL20071_190, allele A of SNP IL2_6411 and allele T of SNP EE_2225. The improved phenotype according to the invention is both an increased yield and an increased amount of soluble sugars allocated to fruits (Brix*Yield) with respect to a plant devoid of said QTL or introgressed sequences. The molecular marker is preferably a SNP marker. The QTL or introgressed sequences are to be found in the deposited seeds NCIMB 42567. The p-value is preferably less than 0.01.

The invention is also directed to the use of at least one of the SNP markers SL10332_112, EP_1592, EP_1027, EP_1150, EP_1876, EE_4621, SL10522_138, EP_0051, IL2_3605, SL20213_779, SL20071_190, IL2_6411 and EE_2225, associated with introgressed sequences or QTL on chromosome 1 conferring the improved phenotype according to the invention, for identifying alternative molecular markers associated with said introgressed sequences, wherein said alternative molecular markers are in the chromosomal region delimited on chromosome 1 by SL10332_112 and EE_2225, or at less than 1 megabase from the locus of at least one of the SNP markers SL10332_112, EP_1592, EP_1027, EP_1150, EP_1876, EE_4621, SL10522_138, EP_0051, IL2_3605, SL20213_779, SL20071_190, IL2_6411 and EE_2225. The alternative molecular markers are preferably associated with said introgressed sequences/QTL with a p-value of 0.05 or less, preferably less than 0.01. The QTL or introgressed sequences are to be found in the deposited seeds NCIMB 42567.

The invention is also directed to a method for identifying a molecular marker associated with a QTL conferring the improved phenotype of the invention, comprising:

identifying a molecular marker in the chromosomal region delimited on chromosome 1 by the SNP markers SL10332_112 and EE_2225, or at less than 1 megabase unit from the locus of at least one of the SNP markers SL10332_112, EP_1592, EP_1027, EP_1150, EP_1876, EE_4621, SL10522_138, EP_0051, IL2_3605, SL20213_779, SL20071_190, IL2_6411 and EE_2225; and determining whether said molecular marker is associated with or linked to the improved phenotype in a segregating population issued from a plant exhibiting said improved phenotype. The population is preferably issued from a plant grown from the deposited seeds NCIMB 42567 or from a progeny thereof, exhibiting the improved phenotype of the invention.

The improved phenotype is both an increased yield and an increased amount of soluble sugars allocated to fruits (Brix*Yield) with respect to a plant devoid of said QTL.

The QTL on chromosome 1 mentioned above, conferring the improved phenotype according to the invention, is the QTL present in HABR1 and in ToPATYIELD (NCIMB 42567).

The molecular markers according to this aspect of the invention are most preferably SNP markers. The invention is also directed to the use of a molecular marker for identifying or selecting a tomato plant comprising, in its genome, a QTL conferring an improved phenotype to *S. lycopersicum* plants, wherein said marker is localized in the chromosomal region delimited on chromosome 1 by the SNP markers SL10332_112 and EE_2225, or at less than 1 megabase unit from the locus of at least one of the SNP markers SL10332_112, EP_1592, EP_1027, EP_1150, EP_1876, EE_4621, SL10522_138, EP_0051, IL2_3605, SL20213_779, SL20071_190, IL2_6411 and EE_2225; and wherein said molecular marker is associated with at least one of the following SNP alleles: allele T of SNP SL10332_112, allele C of SNP EP_1592, allele C of SNP EP_1027, allele G of SNP EP_1150, allele G of SNP EP_1876, allele A of SNP EE_4621, allele G of SNP SL10522_138, allele T of SNP EP_0051, allele T of SNP IL2_3605, allele G of SNP SL20213_779, allele C of SNP SL20071_190, allele A of SNP IL2_6411 and allele T of SNP EE_2225 with a p-value of 0.05 or less, preferably 0.01 or less. The improved phenotype is both an increased yield and an increased amount of soluble sugars allocated to fruits (Brix*Yield) with respect to a plant devoid of said QTL. The molecular marker to be used according to this embodiment is obtainable inter alia by the method for identifying further or alternative molecular markers, as disclosed above. The molecular marker is preferably a SNP marker.

LEGEND OF THE FIGURES

FIG. 1: this figure illustrates the yield of several introgression lines from the population mentioned in example 2. ToPATYIELD is among the few plants having an increased brix*yield compared to the recurrent parent Moneyberg. Brix*yield measurements of individual plans are shown by grey dots, Mean and ANOVA for each introgression line are indicated in rectangles. All rectangles above the horizontal grey line (crossing the Y axes at ~24000) indicate lines with significantly higher brix*yield values (p<0.05).

Figure 2:
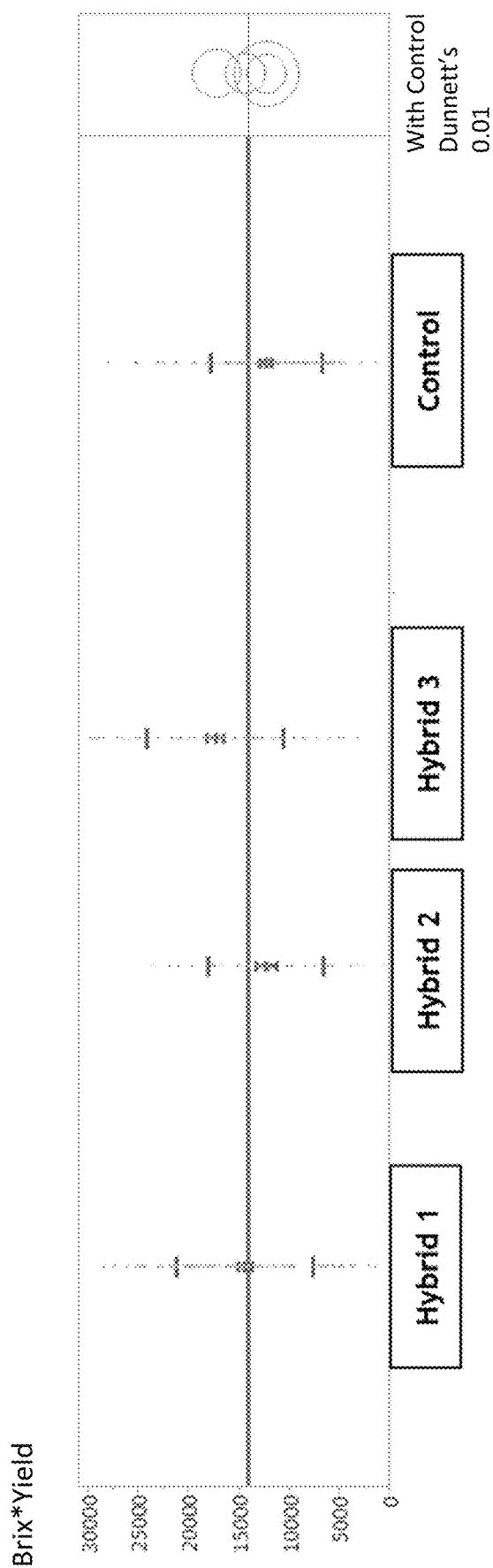

FIG. 2: this figure illustrates the mean values of Brix*Yield for three different hybrids compared to a control corresponding to a cross between HAZ3 (proprietary inbred line of *S. lycopersicum*) and Moneyberg without any wild species DNA. Hybrid 3 was created by crossing HAZ3 and the ToPATYIELD. Hybrids 1 and 2 were created by crossing HAZ3 and other introgression lines carrying a genomic fragment from other wild species at the bottom end of chromosome 1. Only hybrid 3 has a brix*yield which is significantly higher than the control (p<0.01).

EXAMPLES

Example 1: Introgression of a Genomic Fragment from *Lycopersicum pennellii* LA 716 into an Indeterminate *Lycopersicum esculentum* Genetic Background In a first step, a determinate *Lycopersicum esculentum* (=*S. lycopersicum*) plant was created according to the method described by Eshed and Zamir in 1995 with the M82 determinate *Lycopersicum esculentum* as recurrent parent and *Lycopersicum pennellii* LA716 as introgression donor.

As a results of such first step, the M82 *Lycopersicum esculentum* plant obtained contained the expected LA716 introgression fragment on the lower arm of chromosome 1 and showed the expected increase in yield both in inbred or in hybrid combination.

It is well known by the man skilled in the art that the crossing of an inbred determinate line with an inbred indeterminate line produces an indeterminate hybrid plant. As such, in a second step, the M82 *L. esculentum* plant containing the LA716 introgression fragment on the lower arm of chromosome 1 was crossed to a an indeterminate proprietary line, to produce an indeterminate hybrid plant, which yield was measured over three seasons both in South of France and in Israel.

As a check, a hybrid was made between the first M82 inbred not containing the LA716 introgression fragment and the second proprietary inbred line.

There was no yield difference between the two hybrids, demonstrating that the LA716 introgression fragment does not provide any yield increase in an indeterminate *Lycopersicum esculentum* plant.

Example 2: Introgression of a Genomic Fragment from *Lycopersicum Habrochaites*

The present inventors created an introgression line population by crossing a wild species donor *S. habrochaites* (HABR1) and the indeterminate *Lycopersicum esculentum* recurrent parent Moneyberg.

After several backcrosses to the indeterminate recurrent parent Moneyberg, a population made of 62 introgression lines (IL) covering the *S. habrochaites* genome of HABR1 was obtained.

Identification of the *S. habrochaites* Genomic Fragment Affecting Yield

Phenotypic Data:

The IL population was screened for yield. Various parameters affecting yield like flowering time, percentage of fruit set, time for ripening, number of fruits per cluster and the number of ripe clusters in a season were measured during the growth season, in order to identify to what elements might be due an increase in yield.

Fruit weight (i.e. the summed weight of all harvested fruit) and the Total Soluble Solids (TSS) content of fruit were measured immediately after fruit harvest. The yield is measured throughout the growing season: the plants are grown in greenhouses which are visited several times by the inventors who harvested the tomato clusters when 50% of the fruits of a given tomato cluster are ripe. At the end of the growing season, the weight of all fruits is summed, to provide the plant yield. The growing season varies according to local practices, for example in Israel, there are two growing seasons, one from August/September to February/March and a second one from March to August. The plant according to the invention shows a yield increase over the season versus plants not containing the introgression fragment, irrespective of the season or the location.

Brix*Yield value per plant was evaluated by multiplying the total weight of the harvested fruit per plant and the average Total Soluble Solids (TSS) of five ripe fruits per plant, measured by a refractometer. Whereas the parameter thus measured is TSS*Yield, it can be assimilated to Brix*Yield, given the correlation between Brix and TSS, and because the data really informative is the % increase of this TSS*Yield or Brix*Yield and not the absolute level of TSS*Yield or Brix*Yield. The extent of % increase of TSS*Yield and of Brix*Yield are expected to be very similar.

The line called ToPATYIELD was identified as having a higher brix*yield compared to the recurrent parent (Moneyberg) and was selected for further analysis. At this point, the inventors have demonstrated that a *S. habrochaites* genomic fragment from HABR1 (the wild parent) could provide an increase of the brix*yield value in indeterminate tomatoes. The next steps were to identify the genomic fragment responsible for such phenotype.

Molecular Marker Identification:

Genomic DNA from tomato leaves was extracted using Qiagen DNeasy plant DNA extraction kit.

SNP Set Selection

On basis of public domain SNP datasets such as what can be found in EUSOL, in the sol genomics network or in the PGSB Plant Genome and Systems Biology dedicated to tomato, a SNP selection has been performed and a first set of 384 SNP created:

The selection of the SNPs was performed applying the following filter steps:

Filter 1: SNP score and design ability: One SNP per loci/contig was selected, having an Illumina score of 0.7 or higher (in accordance to Illumina's standards).

Filter 2: Repetitiveness: Sequences were BLASTed against plant repetitive sequence databases, and SNPs with hits in these regions were de-selected.

Filter 3: Genotypic information: In cases were genotypic information was available, from public domain resources, SNPs showing no segregation across samples were de-selected.

Filter 4: Unique SNP information: Deselection for the identical SNP/loci derived from different datasets. SNP sequences having more than 90% BLAST overlap were considered as identical.

Filter 5: Genome coverage and distribution: The selected SNPs were inspected for their genome coverage and distribution. This was done by BLAST-placing the SNP sequences in the WGS (Whole Genome Sequencing) and subsequently identifying the chromosome location and SNP position.

SNP Genotyping

High-throughput SNP genotyping was carried out with the GoldenGate assays and the BeadXpress reader from Illumina. The genotypes of the ILs and the two parental lines were screened with the 384 markers in a single plate. SNP genotyping data was scored using the Illumina GenomeStudio genotyping software with a no-call threshold of 0.25.

Illumina GoldenGate Technology Details

A SNP set was designed for the Illumina GoldenGate assay, which used locus and allele-specific oligos with cy3/cy5 labeling to detect SNP alleles at each locus. These custom Oligo Pool Assay (OPA) sets were then run on the Illumina BeadXpress Reader as 384-plex VeraCode assays. Veracode uses cylinder microbeads with an internal barcode to differentiate bead types which correspond to different SNP loci (384 bead types are used for a 384-plex SNP set), and each microbead was coated with oligos that contain a unique address that hybridizes with the labeled products. During scanning on the BeadXpress Reader, the beads were aligned in a groove plate, and the bead codes and cy3/cy5 signal intensities were measured across replicated sets of beads to assign the SNP alleles. This procedure allowed a rapid, high-quality SNP calling of 96 samples by 384 SNPs without requiring fixed arrays. The GenomeStudio software from Illumina was used for clustering alleles based on the ratio of the cy3/cy5 signal intensities to call the three genotype classes. This was done first with the 384 SNP identified, but in order to increase the precision of the analysis, a second additional set of 384 other SNP markers was created, similarly to the process described for the first set, leading to a 768 SNP markers set altogether).

Selection of Polymorphic SNPs

SNPs with call rate below 70% or with no polymorphism between donor and recurrent parents were removed from the analysis, resulting in 353 SNPs that were retained as technically valid and polymorphic markers from the first plate and additional 307 SNPs from the second plate. Altogether 660 SNPs were used for further analysis.

Results:

Association analysis of the ToPATYIELD plant identified a set of markers significantly linked to the yield increase. The list of associated markers and their positions are summarized in table 1. The sequences of these SNPs, including the flanking sequences are reported in table 2 and accompanying sequence listing, part of the application.

Results showed that the locus responsible for the yield increase was located in chromosome 1, on an introgression fragment of 6.271 Mbp, between position 91 778 012 and position 98 049 922, such physical position on the genome being based on the version 2.5 of the tomato genome (Bombarely 2011).

TABLE 1 list of SNPs, their position, and the alleles of the wild parent and recurrent parent

| SNP | SEQ ID No | Position | Moneyberg | ToPATYIELD |
| --- | --- | --- | --- | --- |
| SL10332_112 | 1 | 91778012 | C/C | T/T |
| EP_1592 | 2 | 92005578 | T/T | C/C |
| EP_1027 | 3 | 92495820 | T/T | C/C |
| EP_1150 | 4 | 92738302 | T/T | G/G |
| EP_1876 | 5 | 94343410 | A/A | G/G |
| EE_4621 | 6 | 94819866 | G/G | A/A |
| SL10522_138 | 7 | 95107106 | T/T | G/G |
| EP_0051 | 8 | 95123471 | C/C | T/T |
| IL2_3605 | 9 | 96217112 | G/G | T/T |
| SL20213_779 | 10 | 96487626 | A/A | G/G |
| SL20071_190 | 11 | 97885427 | A/A | C/C |
| IL2_6411 | 12 | 97892448 | C/C | A/A |
| EE_2225 | 13 | 98049922 | C/C | T/T |

TABLE 2 sequences of the SNPs

| SEQ ID | Nom du SNP | Sequence of the SNPs; the allele associated with the yield increase, i.e. the *s. habrochaites* is mentioned second in the bracket |
| --- | --- | --- |
| 1 | SL10332_112 | AGAAACAAATACTTGTTAACAACTTAACATGATGTAATGGTAAATAT GAACACATAGAAA[C/T]GGGGACAAAAAATAAAGGTCTTCTAATGCT CTTCAGATGAAGCAACACTGGTAATGTTAG |
| 2 | EP_1592 | GAGAAAAAGACCATTAGACAAAGAAAAGGTGTTTTGATAGCTACGG AGAAAAAGAGAAAG[T/C]ATAGAGAAAAAAAGCAAAACAGGGAGAT GAAAGGGGTCTCTAATGGGAGATCCATTCCCT |
| 3 | EP_1027 | CTGGACAATTTAGAGCTGAATCTTGATATTCTGCCAATTGCTATGGT AATTGCAGCATCA[T/C]AAGAAGCTCAAAGGCTTAAGGCTTGGAGAT TTACTTCATGGAGTGGGGGGAGATTATGGT |
| 4 | EP_1150 | GTAATAGAGAAACTGAAAGAAAAAAGGGACAAAAATCAAGCTGTCC CGGCATTTACTCTT[T/G]NTTTTCTACCAGCTTTCTCTACTTTTGTCT GATCTTACGAAATGTAACCGCTTCACTCAT |
| 5 | EP_1876 | TGTCTACAAAATGTGGGAGGTACAAAGAGGGATTTGATTTTAGTGC TGAGAGAGTGACTA[A/G]AAGTATTGATGAGAGCTTGGAGAGGCTG CAGCTTGATTATGTTGATATGTTACAATGTCA |
| 6 | EE_4621 | CATCAAAATCCAGAACAAGGAAATGAAACGAAGCTTCTTAGATTGT TCTTCTGAAGATTG[G/A]TCCAACTATTAGTTTGGCCTACTTACAAGT TACCGATTAACTTAAGCTTAGGAAGCGAAT |
| 7 | SL10522_138 | CACAATAAGGTAAACATATCATGCAGTTTGCTGGTTTTGACTCTTAG ATTGAGCAGACAA[T/G]AGGGGGTTGCTGAGGTGGTAAGCACTCTT CACCTCCAACACCAAGGTTGCTGGTAGCAAA |
| 8 | EP_0051 | ACTCATCAGCAAAAGGAACAGAATCTTGGCTTCTGCTCCTGTTTCT TCACCCTTCACTTC[C/T]CCAAATGAAGAGTCCGAAAAAGCTAAGTT AGCTCAGGTTGCCAAAAGACTACTGAATACT |
| 9 | IL2_3605 | CATTAGAGCATCTGGTGGATTCAGAAATTCTTTCACTAAAGCTCATG GAATTTCAAACAC[G/T]ATTGGAATCATCCTTCTTCTGGTATATCCAG TCTGGGCATTGATTCTCCACTTTCTATAA |
| 10 | SL20213_779 | ATTTGTATTTCATCGTAGCAAGTCAGAAGTGTATTTCTGCTTGAAAT GTTTTTTATGTGC[A/G]TTGATTAGTGAAAATACAGAATACTTTCTAA TGGTACACAAAATTATTTTCTTTGTCGAA |
| 11 | SL20071_190 | TGTAATATAATATGCTTCAACAGTATTTATTCAACATATAGCCATTGA TATCATTCAAAC[A/C]AAGCACTCCCAGTTTCGCATAGAGGTACCAT TTAACCAAACTGGAGGAATAAATTATCTC |

TABLE 2-continued sequences of the SNPs

| SEQ ID | Nom du SNP | Sequence of the SNPs; the allele associated with the yield increase, i.e. the *s. habrochaites* is mentioned second in the bracket |
|---|---|---|
| 12 | IL2_6411 | TCAGGAAACTCTTCTTAATCTGCTATTGCGGAATTATCTTCACTACA ACTTGTACGATCA[C/A]GCAGAGAAATTGAGGTCAAAGGCCCCCCA TTTTGAAGCTCATTCAAATCAGCAGTTCTGC |
| 13 | EE_2225 | TTTTCATAGGAAAAAATTGGAGGTTTACAATGAGGTGCTTCGGAGG CTTAAAGAAGAATC[C/T]GACAATAACGACACTTTACAATCTGCTTTT GACGATGAACTTTGGGCTCATTTCAATCGC |

Comparison of Hybrid Combinations:

The Brix*yield value of three hybrids made by crossing introgression lines with an indeterminate proprietary inbred line named HAZ3 was measured similarly to what is described here before.

Hybrid 1 results from the cross of HAZ3 with an introgression line containing a genomic introgression fragment from the bottom arm of chromosome 1 of *S. chmielewskii*, Hybrid 2 results from the cross of HAZ3 with an introgression line containing the chromosome 1 genomic introgression fragment from LA716 while Hybrid 3 results from the cross of HAZ3 with ToPATYIELD introgression line containing the genomic introgression fragment of the present invention.

The resulting indeterminate hybrids were grown at three locations (Hazav and Beit Hanan, Israel and St. Remy, France) during three seasons. As control the present inventors used a cross between HAZ3 and Moneyberg without any wild species DNA (Control). Mean values of Brix*Yield for all hybrids were compared to the control. Only the hybrid with the *S. habrochaites* fragment (Hybrid 3) had a higher Brix*Yield value (p<0.01) (see FIG. 2).

Very interestingly, the genomic fragment in these three IL lines are located in the same region of chromosome 1, but confer different phenotypes, depending on the introgressed sequences and thus introgression donor.

Further Comparison of Hybrid Combinations:

The effect of the *S. habrochaites* introgression fragment is measured on yield, brix and brix*yield by comparing hybrids made by crossing a proprietary inbred line with ToPATYIELD ("hybrid ToPATYIELD") or with the recurrent parent Moneyberg ("hybrid Moneyberg»). Values labeled with * are statistically significant (p<0.01). Combined results of trial conducted over two years at Hazav, Israel and one year at St. Remy, France, are reported in table 3.

TABLE 3

|  | Hybrid Moneyberg | Hybrid ToPATYIELD |
|---|---|---|
| Average fruit weight per plant (kg) | 2.941 | 3.915* |
| Average Brix (%) | 4.03 | 4.22 |
| Average Brix*Yield per plant (%*kg) | 12.431 | 17.488* |

Example 3: Further Breeding and Development of Indeterminate Inbred and Hybrid Plants Creation of BC2S2 Seeds:

The line called ToPATYIELD was crossed with a proprietary indeterminate breeding line to create BC2S2 seeds as described hereafter: the line ToPATYIELD is crossed once with the proprietary indeterminate breeding line and the resulting plant is backcrossed two times to the proprietary indeterminate breeding line. The BC2 plant is self-pollinated once to obtain a BC2S1 and plant which is itself self-pollinated to obtain the BC2S2 seeds.

One will note that the presence of the *S. habrochaites* genomic fragment is followed through the breeding steps by the use of the molecular markers described here before, especially IL2_6411 and IL2_3605.

Creation of Two New Indeterminate Inbred Lines:

The BC2S2 plants containing the introgression fragment from *S. habrochaites* on chromosome 1 has been used in crosses with two independent, unrelated indeterminate breeding lines, HAZ Line 1 and HAZ Line 2, generally used for producing indeterminate hybrid tomato plants with round fruits of about 150-200 grams.

In both cases, the BC2S2 plants are crossed once with the HAZ 1 or to the HAZ 2 line, followed by four backcrosses and a self, leading to two indeterminate BC4S1 plants, HAZ-1-BC4S1-ToPATYIELD and HAZ-2-BC4S1-ToPATYIELD, having the genetic background of HAZ-1 or HAZ-2 indeterminate plants and the introgression fragment from *S. habrochaites* on chromosome 1. Similarly to the creation of the BC2S2 plants, the introgression fragment from *S. habrochaites* on chromosome 1 is followed through the breeding steps by the use of the molecular markers.

Creation of Four Indeterminate Hybrids:

The two indeterminate BC4S1 plants, HAZ-1-BC4S1-ToPATYIELD and HAZ-2-BC4S1-ToPATYIELD, having the introgression fragment from *S. habrochaites* on chromosome 1 were crossed with proprietary inbred lines HAZ-A and HAZ-B to create two new hybrids.

In parallel, lines HAZ-1 and HAZ-2 were also crossed with HAZ-A and HAZ-B, so that the hybrids resulting from the various crosses could be compared.

Table 4 below summarizes the name of the hybrids and of the parents and specifies the hybrids having the introgression fragments.

TABLE 4

|  | HAZ-A | HAZ-B |
|---|---|---|
| HAZ-1 | Hybrid 1 | / |
| HAZ-1-BC4S1-ToPATYIELD | Hybrid 1 having the introgression fragment | / |
| HAZ-2 | / | Hybrid 2 |
| HAZ-2-BC4S1-ToPATYIELD | / | Hybrid 2 having the introgression fragment |

All four hybrids were grown in Yad Natan, Israel, in a greenhouse with drip irrigation system under standard winter growing conditions (from September with planting to February at final harvest. Day length is between 10 and 12 hours of light per day and average temperature in ° C. is based on data from the Israeli Meteorological Services, see table 5).

TABLE 5

| Month | Average low | Average high |
|---|---|---|
| September | 19.5 | 31.5 |
| October | 16.7 | 28.5 |
| November | 12.5 | 23.5 |
| December | 8.9 | 18.8 |
| January | 7.6 | 16.7 |
| February | 7.5 | 17.5 |

Tomato clusters were harvested when 50% of the fruits of a cluster were ripe (full red). The number of fruits on each plants and individual fruit weight in grams were recorded for each cluster. Total yield was calculated as the sum of all individual fruits. Fruit total soluble solid was measured for up to three red fruits per cluster with a digital refractometer. In view of the similarity of these parameters, Brix*Yield (last column) is assimilated to Yield x TSS.

Results are given in table 6 and 7, for two years, (*) indicates statistically significant results (n=15; P<0.05).

TABLE 6

Result obtained for Year 1

| Year 1 | number of fruit/plant | fruit size (gr) | Yield (g/plant) | TSS | Brix*Yield |
|---|---|---|---|---|---|
| Hybrid 1 | 24 | 191.2 | 3100 | 4.008 | 12430 |
| Hybrid 1 introgression fragment | 26 | 208.2 | 3900* | 3.930 | 15330* |
| Hybrid 2 | 30 | 134.7 | 2450 | 4.055 | 9940 |
| Hybrid 2 introgression fragment | 37* | 129.1 | 3310* | 3.863 | 12790* |

TABLE 7

Result obtained for Year 2

| Year 2 | number of fruit/plant | fruit size (gr) | Yield (g/plant) | TSS | Brix*Yield |
|---|---|---|---|---|---|
| Hybrid 1 | 23 | 140.6 | 3200 | 4.04 | 12930 |
| Hybrid 1 introgression fragment | 24.9 | 155* | 3900* | 4.3 | 16770* |
| Hybrid 2 | 27.4 | 107 | 2890 | 4.23 | 12250 |
| Hybrid 2 introgression fragment | 31.1 | 112.4 | 3480* | 4.07 | 14160* |

These tables clearly show that all hybrids having the introgression fragment have an increased yield and an increased Brix*Yield, with respect to the corresponding hybrids not having the introgression fragment.

Moreover, it can be observed that the increased yield and increased Brix*Yield is not accompanied by a statistically significant decrease of the brix (TSS).

Example 4: Introgression of a Genomic Fragment from Lycopersicum hirsutum LA1777 into an Indeterminate Lycopersicum esculentum Genetic Background The Monforte et al, 2000 publication discloses tomato plants, comprising an introgression fragment from the *S. habrochaites* accession LA1777 on chromosome 1, allegedly imparting increased yield and brix*yield of the plants, especially at the heterozygous stage. This document however only relates and describes tomato plants having determinate growth habits.

In order to assess the possibility to use the LA1777 introgression in indeterminate tomatoes, so that it can also confer the same increased yield and brix*yield phenotype not only in determinate tomatoes, but also in indeterminate ones, the present inventors assessed the brix*yield increase in a hybrid cross leading to a tomato plant with an indeterminate habit by crossing a plant carrying the LA1777 introgression (namely the Near Isogenic Line TA523 referred to in Monforte et al) with an indeterminate line (4131).

As a control, a hybrid cross was made between the very same plant not carrying the LA1777 introgression (namely from line E6203, as TA523 is a NIL comprising a single introgression from LA1777) and the same indeterminate line (4131).

All growth, harvest and phenotyping were done as described in example 3. Tomato clusters were harvested when 50% of the fruits of a cluster were ripe (full red). The number of fruits on each plants and individual fruit weight in grams were recorded for each cluster. Total yield was calculated as the sum of all individual fruits (gram per plant). Fruit total soluble solid was measured for up to three red fruits per cluster with a digital refractometer. In view of the similarity of these parameters, Brix*Yield (last column) is assimilated to Yield x TSS. The trial included three replicates of five plants per genotype (i.e. a total of 15 plants per genotype), and seven clusters.

The results are presented in table 8.

TABLE 8

Brix*Yield summary (i.e. total fruit weight multiplied by sugar content total amount of carbohydrates allocated to the fruit)

| | Brix*Yield for E6203 x 4131 | Brix*Yield for TA523 x 4131 |
|---|---|---|
| Cluster 1 | 3068.73 | 2797.76 |
| Cluster 2 | 2407.72 | 3181.39 |
| Cluster 3 | 2932.89 | 2955.12 |
| Cluster 4 | 3652.37 | 3541.73 |
| Cluster 5 | 3704.32 | 3839.68 |
| Cluster 6 | 3165.55 | 3651.9 |
| Cluster 7 | 2962.12 | 1969.73 |
| Mean of the clusters | 21893.7 | 21937.31 |

The data clearly demonstrate that the LA1777 introgression does NOT lead to any statistically significant brix*yield increase in tomatoes having an indeterminate growth habit.

REFERENCES

Bernacchi et al. 1998a. Advanced backcross QTL analysis in tomato. I. Identification of QTLs for traits of agronomic importance from *Lycopersicum hirsutum*. Theor. Appl. Genet. 97: 381-397

Bernacchi et al. 1998b Advanced backcross QTL analysis of tomato. II. Evaluation of near-isogenic lines carrying single-donor introgressions for desirable wild QTL-allele derived from *Lycopersicum hirsutem* and *L. pimpinellifolium*. Theor. Appl. Genet. 97: 170-180

Eshed and Zamir 1995, An introgression line population of *Lycopersicum pennellii* in the cultivated tomato enables the identification and fine mapping of yield-associated QTL. Genetics 141: 1147-1162

Eshed and Zamir. 1996. Less-than-additive epistatic interactions of quantitative trait loci in tomato. Genetics 143 1807-1817.

Monforte A. J. & Tanksley S. D. 000. Fine mapping of a quantitative trait locus (QTL) from *Lycopersicon hirsutum* chromosome 1 affecting fruit characteristics and agronomic traits: breaking linkage among QTLs affecting different traits and dissection of heterosis for yield. Theor Appl Genet 100:471-479.

Stevens, M., and Rick, C. M. 1986. Genetics and Breeding. In: The Tomato Crop. A scientific basis for improvement, pp. 35-109. Atherton, J., Rudich, G. (eds.). Chapman and Hall, New York.

The invention claimed is:

1. A *Solanum lycopersicum* plant comprising in its genome, on chromosome 1, introgressed sequences from *Solanum habrochaites*, wherein said introgressed sequences confer on the plant an improved phenotype in terms of both an increased fruit yield and an increased amount of soluble sugars allocated to fruits relative to a *Solanum lycopersicum* plant devoid of said introgressed sequences, and wherein said introgressed sequences (a) are present in the chromosomal region of chromosome 1 of said *Solanum lycopersicum* plant beginning with the nucleotide identified as SNP SL10332_112 located at position 61 of SEQ ID NO: 1 and extending through the chromosomal region to SEQ ID NO: 13 ending with the nucleotide identified as SNP EE_2225 located at position 61 of SEQ ID NO: 13; and (b) are *Solanum habrochaites* sequences present in the chromosomal region of chromosome 1 of deposited *Solanum lycopersicum* seeds having NCIMB accession number 42567, beginning with the nucleotide identified as SNP SL10332_112 located at position 61 of SEQ ID NO: 1 and extending through the chromosomal region to SEQ ID NO: 13 ending with the nucleotide identified as SNP EE_2225 located at position 61 of SEQ ID NO: 13.

2. The *S. lycopersicum* plant according to claim 1, having no statistically significant decrease in total soluble solids relative to a *S. lycopersicum* plant devoid of said introgressed sequences.

3. The *S. lycopersicum* plant according to claim 1, wherein said plant is indeterminate.

4. The *S. lycopersicum* plant according to claim 1, wherein the introgressed sequences from *S. habrochaites* are heterozygously present in the genome of the plant.

5. The *S. lycopersicum* plant according to claim 1, characterized by the presence in the genome of said *S. lycopersicum* plant of the following alleles:
   allele T at position 61 of SEQ ID No.1,
   allele C at position 61 of SEQ ID No.2,
   allele C at position 61 of SEQ ID No.3,
   allele G at position 61 of SEQ ID No.4,
   allele G at position 61 of SEQ ID No.5,
   allele A at position 61 of SEQ ID No.6,
   allele G at position 61 of SEQ ID No.7,
   allele T at position 61 of SEQ ID No.8,
   allele T at position 61 of SEQ ID No.9,
   allele G at position 61 of SEQ ID No.10,
   allele C at position 61 of SEQ ID No.11,
   allele A at position 61 of SEQ ID No.12 and
   allele T at position 61 of SEQ ID No.13.

6. The plant according to claim 1, wherein said plant is a progeny of seeds of NCIMB accession number 42567.

7. A plant part of the *S. lycopersicum* plant according to claim 1, wherein said plant part comprises cells comprising in their genome on chromosome 1 the introgressed sequences from *S. habrochaites* conferring the improved phenotype.

8. Seed of a *S. lycopersicum* plant, giving rise when grown up to the plant according to claim 1.

9. A tissue culture of regenerable cells of the plant according to claim 1, wherein the regenerable cells are from embryos, protoplasts, meristematic cells, callus, pollen, leaves, anthers, stems, petioles, roots, root tips, seeds, flowers, cotyledons, and/or hypocotyls, and contain in their genome the introgressed sequences from *S. habrochaites* on chromosome 1 conferring the improved phenotype.

10. The plant part according to claim 7, wherein the presence of said introgressed sequences on chromosome 1 is characterized by
   the presence of allele T at position 61 of SEQ ID No.9 and
   the presence of allele A at position 61 of SEQ ID No.12.

11. A method for detecting and/or selecting *S. lycopersicum* plants according to claim 1, said method comprising detecting of the following markers: allele T at position 61 of SEQ ID No.1, allele C at position 61 of SEQ ID No.2, allele C at position 61 of SEQ ID No.3, allele G at position 61 of SEQ ID No.4, allele G at position 61 of SEQ ID No.5, allele A at position 61 of SEQ ID No.6, allele G at position 61 of SEQ ID No.7, allele T at position 61 of SEQ ID No.8, allele T at position 61 of SEQ ID No.9, allele G at position 61 of SEQ ID No.10, allele C at position 61 of SEQ ID No.11, allele A at position 61 of SEQ ID No.12 and allele T at position 61 of SEQ ID No.13, in a genetic material sample of the plant to be selected, whereby the presence of the markers allows for detecting and/or selecting of said plant.

* * * * *